(12) United States Patent
Takizawa

(10) Patent No.: US 11,219,382 B2
(45) Date of Patent: Jan. 11, 2022

(54) HEARTBEAT MEASUREMENT DEVICE

(71) Applicant: Murata Manufacturing Co., Ltd., Kyoto (JP)

(72) Inventor: Koichi Takizawa, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 142 days.

(21) Appl. No.: 16/797,780

(22) Filed: Feb. 21, 2020

(65) Prior Publication Data

US 2020/0260974 A1    Aug. 20, 2020

Related U.S. Application Data

(63) Continuation of application No. PCT/JP2018/026205, filed on Jul. 11, 2018.

(30) Foreign Application Priority Data

Aug. 31, 2017 (JP) ............................. JP2017-167060

(51) Int. Cl.
*A61B 5/024*  (2006.01)
*A61B 5/00*  (2006.01)
*G01S 13/88*  (2006.01)

(52) U.S. Cl.
CPC ........ *A61B 5/02444* (2013.01); *A61B 5/6893* (2013.01); *A61B 5/726* (2013.01);
(Continued)

(58) Field of Classification Search
None
See application file for complete search history.

(56) References Cited

U.S. PATENT DOCUMENTS

2005/0253742 A1    11/2005  Soga
2008/0195338 A1*   8/2008   Geisheimer ............. G01S 7/415
                                                              702/77
(Continued)

FOREIGN PATENT DOCUMENTS

CN       1698333 A    11/2005
CN    101553163 A    10/2009
(Continued)

OTHER PUBLICATIONS

International Search Report for International Application No. PCT/JP2018/026205 dated Aug. 14, 2018.
(Continued)

*Primary Examiner* — Yi-Shan Yang
(74) *Attorney, Agent, or Firm* — Pearne & Gordon LLP

(57) ABSTRACT

A heartbeat measurement device includes a transmitter configured to transmit a transmission signal from a transmission antenna to a person to be measured, a receiver configured to receive a signal reflected from the person to be measured as a reception signal using a reception antenna, and an orthogonal detection circuit configured to generate an I signal that is an in-phase component of the transmission signal and the reception signal and a Q signal that is a quadrature component of the transmission signal and the reception signal. The heartbeat measurement device further includes a Fourier transform unit configured to calculate a spectrum in positive and negative frequency domains on the basis of the I signal and the Q signal and a signal processing unit configured to compare positive and negative frequency components in the spectrum to extract a heartbeat component.

15 Claims, 7 Drawing Sheets

(52) U.S. Cl.
CPC ........ *A61B 5/7257* (2013.01); *A61B 2503/22* (2013.01); *G01S 13/88* (2013.01)

(56) References Cited

U.S. PATENT DOCUMENTS

| | | | |
|---|---|---|---|
| 2009/0062654 A1* | 3/2009 | Zhang | G01S 7/5205 |
| | | | 600/455 |
| 2009/0240133 A1 | 9/2009 | Friedman et al. | |
| 2014/0155729 A1 | 6/2014 | Saitoh | |
| 2015/0327774 A1 | 11/2015 | Kim et al. | |
| 2016/0173317 A1* | 6/2016 | Bitton | H04L 27/364 |
| | | | 455/114.2 |
| 2016/0338652 A1 | 11/2016 | Yoshioka et al. | |
| 2017/0052238 A1 | 2/2017 | Le Fur | |
| 2017/0150929 A1 | 6/2017 | Sankai | |
| 2018/0042499 A1 | 2/2018 | Sato | |

FOREIGN PATENT DOCUMENTS

| | | |
|---|---|---|
| EP | 3 167 801 A1 | 5/2017 |
| JP | 2006-55504 A | 3/2006 |
| JP | 2014-039838 A | 3/2014 |
| JP | 2014-042722 A | 3/2014 |
| JP | 2016-013239 A | 1/2016 |
| JP | 2016-136716 A | 7/2016 |
| JP | 2016-214876 A | 12/2016 |
| JP | 2017-501413 A | 1/2017 |
| WO | 2013/042786 A1 | 3/2013 |
| WO | 2016/006468 A1 | 1/2016 |
| WO | 2016/140367 A1 | 9/2016 |

OTHER PUBLICATIONS

Written Opinion for International Application No. PCT/JP2018/026205 dated Aug. 14, 2018.

* cited by examiner

COUNTERCLOCKWISE ROTATION

CLOCKWISE ROTATION

LINEAR MOVEMENT

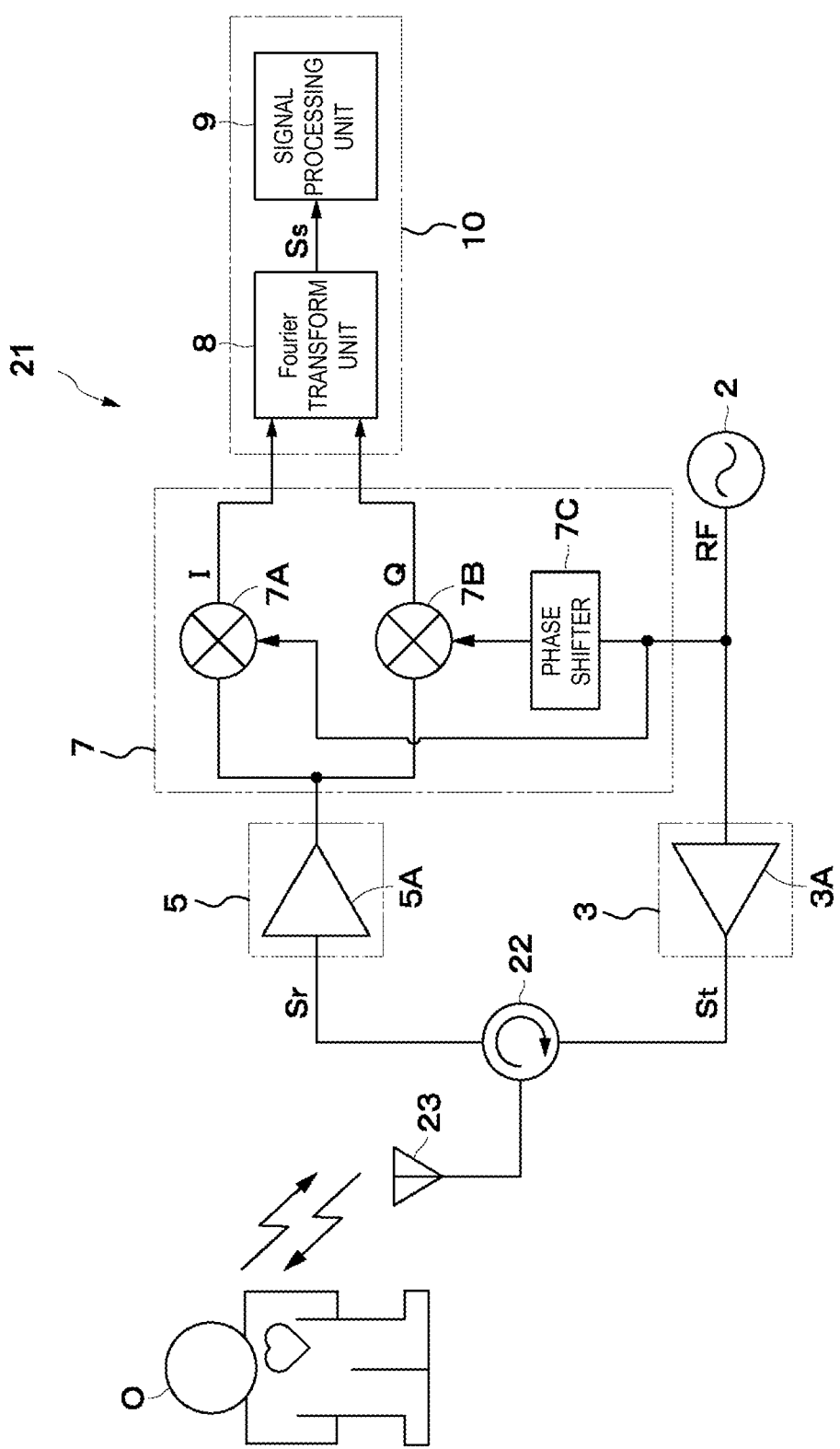

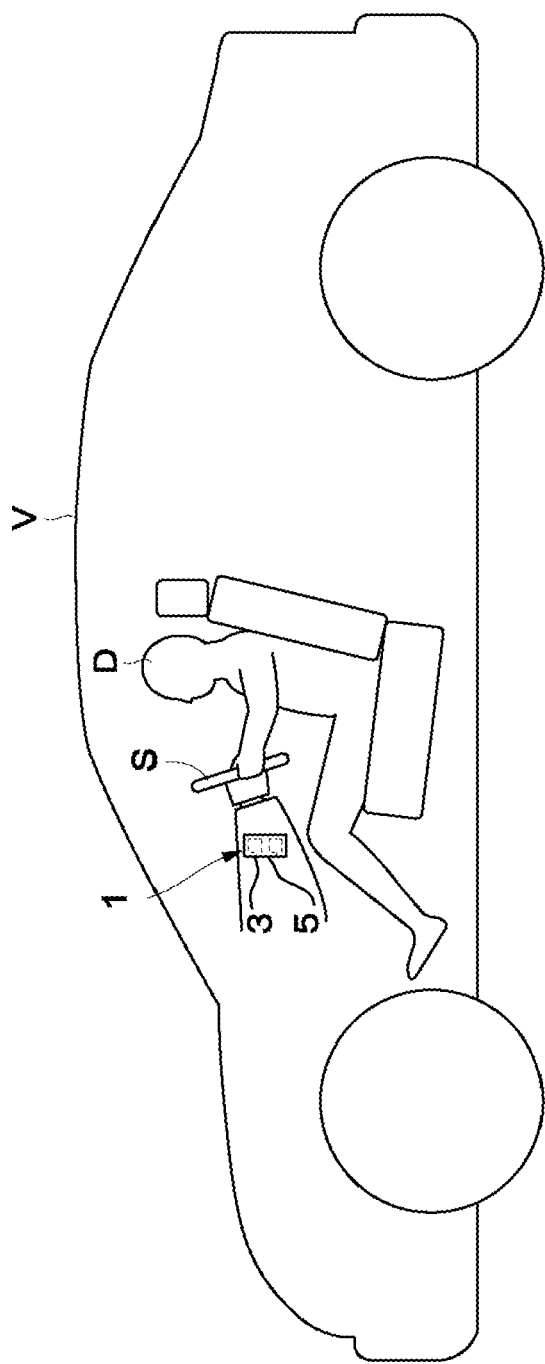

HEARTBEAT MEASUREMENT DEVICE

This is a continuation of International Application No. PCT/JP2018/026205 filed on Jul. 11, 2018 which claims priority from Japanese Patent Application No. 2017-167060 filed on Aug. 31, 2017. The contents of these applications are incorporated herein by reference in their entireties.

BACKGROUND

Technical Field

The present disclosure relates to a heartbeat measurement device suitable for use in measuring the heartbeat of, for example, a human body.

Examples of a heartbeat measurement device include a Doppler sensor utilizing a Doppler effect (see, for example, Patent Documents 1 to 3). Such a Doppler sensor includes a transmission unit for transmitting a transmission signal from a transmission antenna to a person to be measured, a reception unit for receiving a signal reflected from the person to be measured as a reception signal using a reception antenna, and a signal generation unit for generating an I signal that is the in-phase component of the transmission signal and the reception signal and a Q signal that is the quadrature component of the transmission signal and the reception signal.

Patent Document 1 discloses a configuration with which a heartbeat and a breath are calculated by performing a Fourier transform upon an intermediate-frequency signal (IF signal) output from a Doppler sensor and performing filter processing upon a resultant signal.

Patent Document 2 discloses a configuration with which a reflected wave is subjected to IQ detection (orthogonal detection), a heartbeat signal is extracted from time-series data on the norm of a position vector of an acquired signal on an IQ plane, and a heartbeat signal corresponding to a single heartbeat is detected on the basis of the periodic change in the waveform of the extracted heartbeat signal.

Patent Document 3 discloses a Doppler sensor for detecting a heartbeat on the basis of the change in a reflection factor which occurs because of a blood flow. Patent Document 3 discloses a configuration with which, on the basis of two signals corresponding to an amplitude component and a phase component detected by the Doppler sensor, a component based on the body motion of a human body is separated from the amplitude component to extract only a heartbeat.

Patent Document 1: Japanese Unexamined Patent Application Publication No. 2016-13239

Patent Document 2: Japanese Unexamined Patent Application Publication No. 2014-39838

Patent Document 3: Japanese Unexamined Patent Application Publication No. 2006-55504

BRIEF SUMMARY

The cardiopulmonary function monitoring device disclosed in Patent Document 1 calculates a heartbeat and a breath by performing filter processing upon a signal that has been subjected to Fourier transform. Accordingly, there is a problem that a heartbeat and a breath cannot be detected in a case where a frequency component based on a heartbeat and a frequency component based on body motion overlap each other.

The Doppler sensor disclosed in Patent Document 2 checks time-series motion on an IQ plane. In a case where there is noise, the detection of a signal therefore cannot be detected.

The Doppler sensor disclosed in Patent Document 3 detects a heartbeat on the basis of the change in a reflection factor which occurs because of a blood flow. However, since the change in a reflection factor which occurs because of a blood flow is very small, the Doppler sensor is susceptible to noise. Accordingly, there is a problem that body motion and a heartbeat cannot be separated unless the body motion is very small.

The present disclosure provides a heartbeat measurement device capable of accurately extracting a heartbeat component.

A heartbeat measurement device according to the present disclosure including a transmission unit configured to transmit a transmission signal from a transmission antenna to a person to be measured, a reception unit configured to receive a signal reflected from the person to be measured as a reception signal using a reception antenna, and a signal generation unit configured to generate an I signal that is an in-phase component of the transmission signal and the reception signal and a Q signal that is a quadrature component of the transmission signal and the reception signal includes a spectrum computation unit configured to calculate a spectrum in positive and negative frequency domains on the basis of the I signal and the Q signal and a signal processing unit configured to compare positive and negative frequency components in the spectrum to extract a heartbeat component.

According to the present disclosure, a heartbeat component can be accurately extracted.

BRIEF DESCRIPTION OF THE SEVERAL VIEWS OF THE DRAWINGS

FIG. 6 is a block diagram illustrating the configuration of a heartbeat measurement device according to a third embodiment of the present disclosure.

FIG. 7 is a diagram describing a state in which a heartbeat measurement device according to the present disclosure is installed in a vehicle.

DETAILED DESCRIPTION

A heartbeat measurement device according to an embodiment of the present disclosure will be described in detail below with reference to the accompanying drawings.

Figure 1:
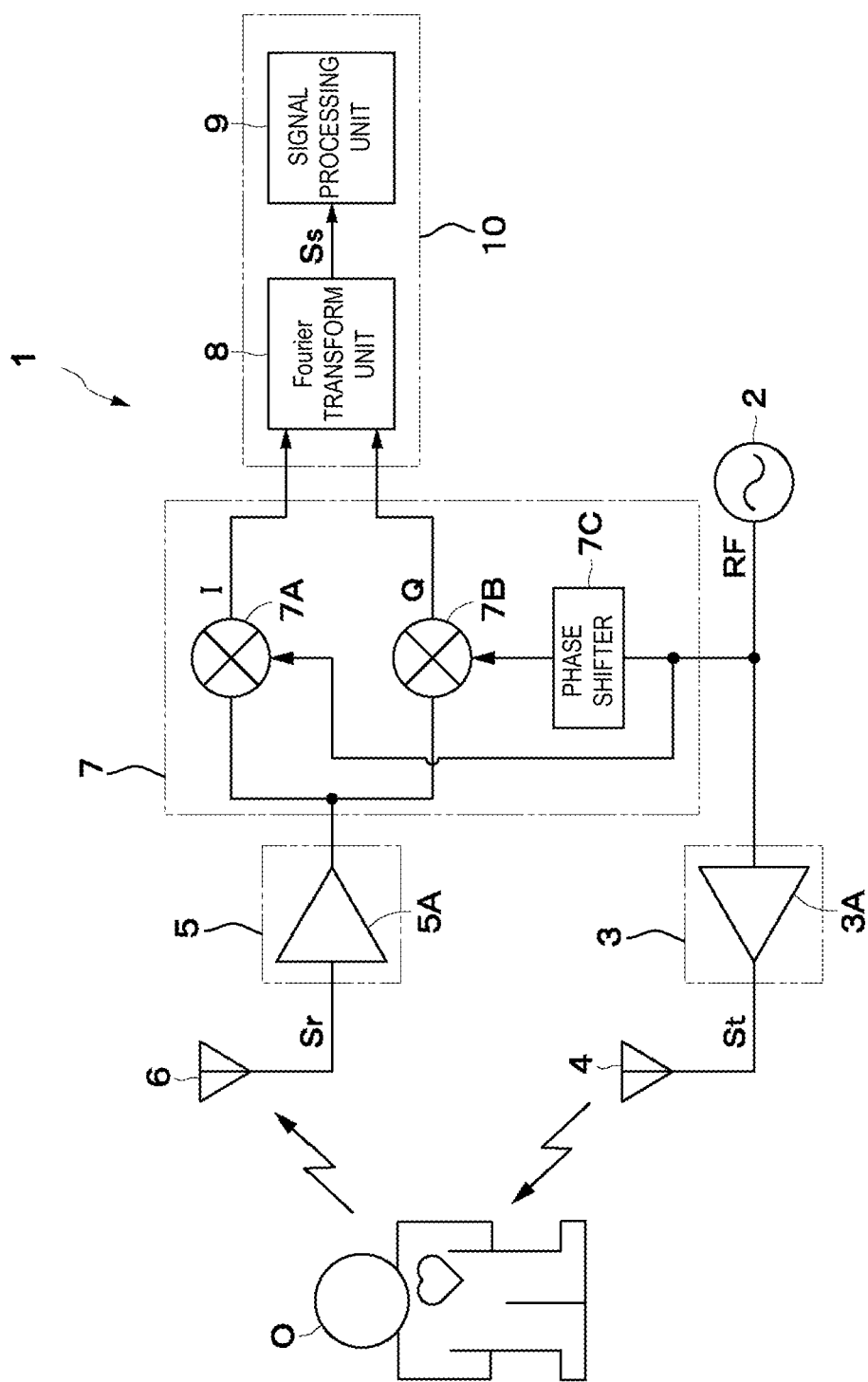
FIG. 1 is a block diagram illustrating the configuration of a heartbeat measurement device according to a first embodiment of the present disclosure.

FIG. 1 illustrates a heartbeat measurement device 1 according to a first embodiment. The heartbeat measurement device 1 includes a transmitter 3, a receiver 5, an orthogonal detection circuit 7, a Fourier transform unit 8, a signal processing unit 9, and other components. The transmitter 3 and the orthogonal detection circuit 7 are connected to a local oscillator 2. The heartbeat measurement device 1 is a Doppler sensor utilizing a Doppler effect and measures the heartbeat of a person to be measured O (human body) in a noncontact manner.

The local oscillator 2 generates an RF signal (high-frequency signal) of a single frequency f0. The frequency f0 of an RF signal is set in the range of 10 GHz to 100 GHz.

The transmitter 3 forms a transmission unit for transmitting a transmission signal St from a transmission antenna 4 to the person to be measured O. The transmitter 3 includes a power amplifier 3A (PA). The input side of the power amplifier 3A is connected to the local oscillator 2. The output side of the power amplifier 3A is connected to the transmission antenna 4. The transmitter 3 amplifies the power of an RF signal generated by the local oscillator 2 using the power amplifier 3A and transmits the RF signal from the transmission antenna 4 to the person to be measured O as the transmission signal St.

The transmission antenna 4 includes various antennas from which the transmission signal St can be emitted. The input side of the transmission antenna 4 is connected to the transmitter 3 (the power amplifier 3A). The transmission antenna 4 is placed, for example, in front of the person to be measured O and emits the transmission signal St input from the transmitter 3 to the chest portion of the person to be measured O.

The receiver 5 forms a reception unit for receiving a signal reflected from the person to be measured O as a reception signal Sr using a reception antenna 6. The receiver 5 includes a low-noise amplifier 5A (LNA). The input side of the low-noise amplifier 5A is connected to the reception antenna 6. The output side of the low-noise amplifier 5A is connected to the orthogonal detection circuit 7. When the transmission signal St is reflected from the person to be measured O, the receiver 5 receives a reflected wave as the reception signal Sr using the reception antenna 6. The receiver 5 amplifies the reception signal Sr using the low-noise amplifier 5A and outputs the reception signal Sr to the orthogonal detection circuit 7.

The reception antenna 6 has a configuration similar to that of the transmission antenna 4. Like the transmission antenna 4, the reception antenna 6 is placed, for example, in front of the person to be measured O and receives a reflected wave at the time of reflection of the transmission signal St from the person to be measured O as the reception signal Sr. The reception antenna 6 includes various antennas capable of receiving the reception signal Sr.

The transmission antenna 4 and the reception antenna 6 do not necessarily have to be placed in front of the person to be measured O and may be at any position (for example, behind the person to be measured O) on condition that a Doppler effect occurs in the reception signal Sr because of the heartbeat of the person to be measured O.

The orthogonal detection circuit 7 forms a signal generation unit for generating an I signal that is the in-phase component of the transmission signal St and the reception signal Sr and a Q signal that is the quadrature component of the transmission signal St and the reception signal Sr. The orthogonal detection circuit 7 performs orthogonal detection upon the reception signal Sr. The orthogonal detection circuit 7 includes mixers 7A and 7B and a phase shifter 7C. The mixer 7A is connected to the local oscillator 2. The mixer 7A mixes the reception signal Sr and an RF signal generated by the local oscillator 2 to output an I signal (in-phase signal). The mixer 7B is connected to the local oscillator 2 via the phase shifter 7C for shifting the phase of an RF signal by 90°. The mixer 7B mixes the reception signal Sr and an RF signal that has passed through the phase shifter 7C to output a Q signal (quadrature signal). The orthogonal detection circuit 7 outputs an I signal and a Q signal to the Fourier transform unit 8.

The Fourier transform unit 8 and the signal processing unit 9 are formed by, for example, an arithmetic device 10 such as a microcomputer. The arithmetic device 10 includes an AD converter (not illustrated) for converting an I signal and a Q signal into digital signals. The arithmetic device 10 further includes a storage unit (not illustrated) storing various programs. The arithmetic device 10 may be embodied as at least one processor that executes various programs to operate as the Fourier transform unit 8 and the signal processing unit 9.

Figure 4:
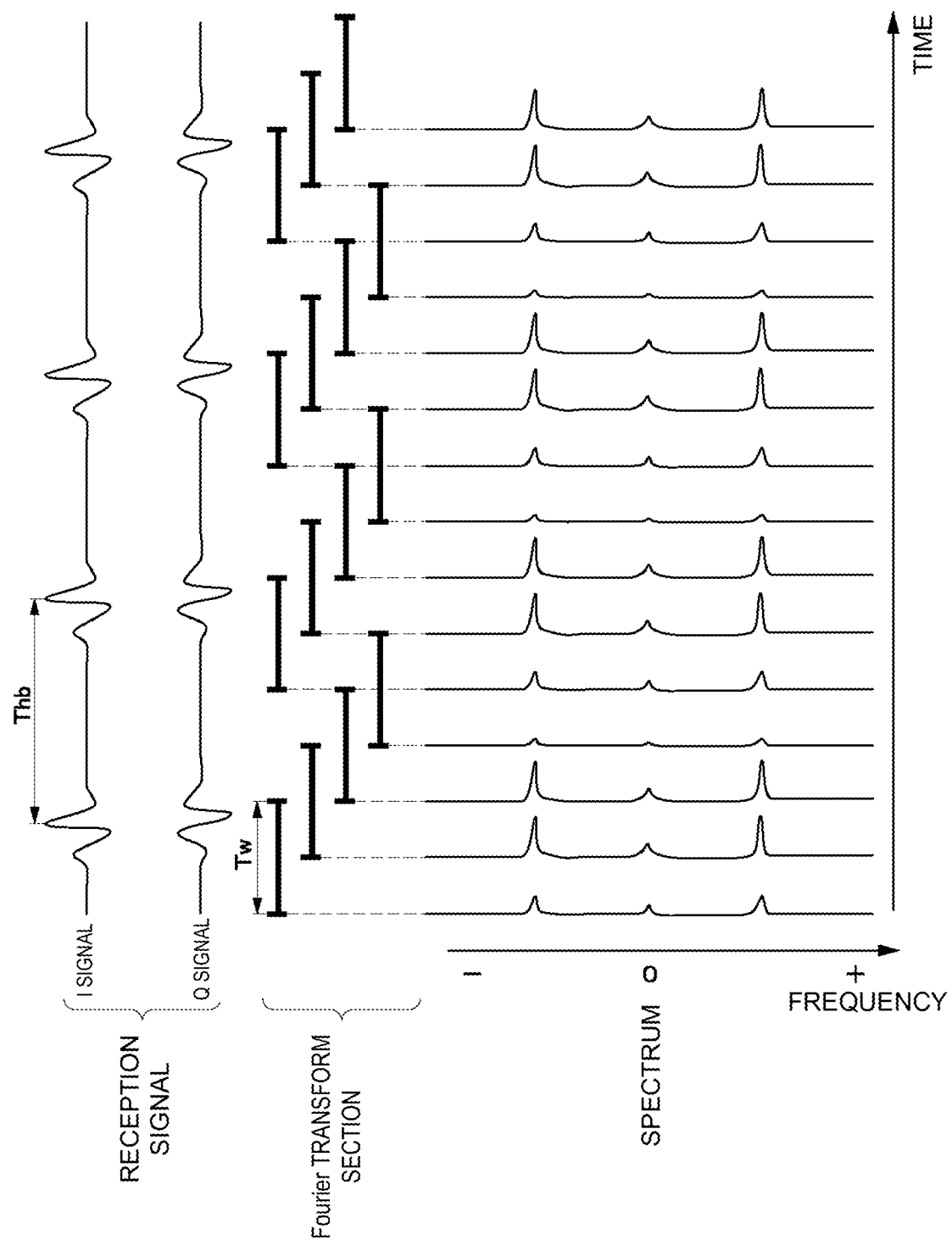
FIG. 4 is a diagram describing the relationship among a reception signal, a Fourier transform section, and a spectrum.

The Fourier transform unit 8 forms a spectrum computation unit for calculating a spectrum Ss in positive and negative frequency domains on the basis of an I signal and a Q signal. The Fourier transform unit 8 sets a time width Tw shorter than a heartbeat interval Thb and Fourier transforms an I signal and a Q signal. Accordingly, an I signal and a Q signal are input into the Fourier transform unit 8, are divided by the time width Tw determined in advance, and are subjected to Fourier transform. As illustrated in FIG. 4, the Fourier transform unit 8 slightly shifts the divided time widths Tw, performs Fourier transform in each segment, and computes the time change in the spectrum Ss. The shift amount of the time width Tw is shorter than the time width Tw (for example, the half of the time width Tw).

The normal value of a heartbeat is, for example, approximately 60 to 100 beats per minute. At that time, the heartbeat interval Thb is, for example, approximately 0.6 to 1 seconds. The Fourier transform unit 8 therefore sets the time width Tw of, for example, approximately 0.3 to 0.5 seconds as a value less than the heartbeat interval Thb, divides an I signal and a Q signal by the time width Tw, and performs Fourier transform.

Data that has been subjected to Fourier transform has positive and negative frequency domains. The Fourier transform unit 8 calculates a frequency component included in respective signals in a certain period of time (the time width Tw) and continuously outputs the time change in the frequency component. The Fourier transform unit 8 outputs the spectrum Ss to the signal processing unit 9.

The signal processing unit 9 compares positive and negative frequency components in the spectrum Ss with each other and extracts a heartbeat component. The signal processing unit 9 analyzes the time change in the spectrum Ss and compares positive and negative frequency components with each other. Specifically, the signal processing unit 9 compares positive and negative signal intensities in the spectrum Ss at the same frequency. When the difference between them is less than or equal to, for example, 20%, that is, one of signal intensities (for example, on a positive side) is in the range of ±20% of the other one of them (for example, on a negative side), the signal processing unit 9 determines that the signal intensities are in the same range. On the other hand, when the difference between them exceeds, for example, 20%, the signal processing unit 9 determines that the signal intensities are in the different ranges. The signal processing unit 9 extracts a signal having positive and negative frequency components whose signal intensities are in the same range as a heartbeat signal.

This signal intensity range is not limited to the above exemplary range and is set as appropriate on the basis of, for example, an actual measurement result. The Fourier transform unit 8 and the signal processing unit 9 are realized by the computation processing of the arithmetic device 10 as described above, but may be formed by respective hardware processing circuits.

Next, the heartbeat measurement operation of the heartbeat measurement device 1 according to this embodiment will be described with reference to FIGS. 1 to 4.

The heartbeat measurement device 1 is placed at, for example, a distance of several meters from the person to be measured O. The heartbeat measurement device 1 outputs the transmission signal St (RF signal) from the transmission antenna 4 to the person to be measured O and receives a reflected wave (RF signal) that has been reflected and transmitted back thereto from the person to be measured O as the reception signal Sr using the reception antenna 6. At that time, a Doppler effect occurs in the reflected wave in response to the movement of the person to be measured O and a phase shift based on the movement of the person to be measured O is produced. The reception signal Sr is down-converted by the mixers 7A and 7B in the orthogonal detection circuit 7, so that an I signal and a Q signal are generated. An I signal and a Q signal are represented by the following mathematics 1 and 2 in which A(t) represents an amplitude, f0 represents the frequency of a transmission signal, d(t) represents the distance between the heartbeat measurement device 1 and the person to be measured O, c represents a speed of light, and φ(t) represents a phase shift caused by noise or the like.

$$I(t) = A(t)\cos\left(\frac{4\pi f0 d(t)}{c} + \phi(t)\right)$$ [Math. 1]

$$Q(t) = A(t)\sin\left(\frac{4\pi f0 d(t)}{c} + \phi(t)\right)$$ [Math. 2]

Figure 2:
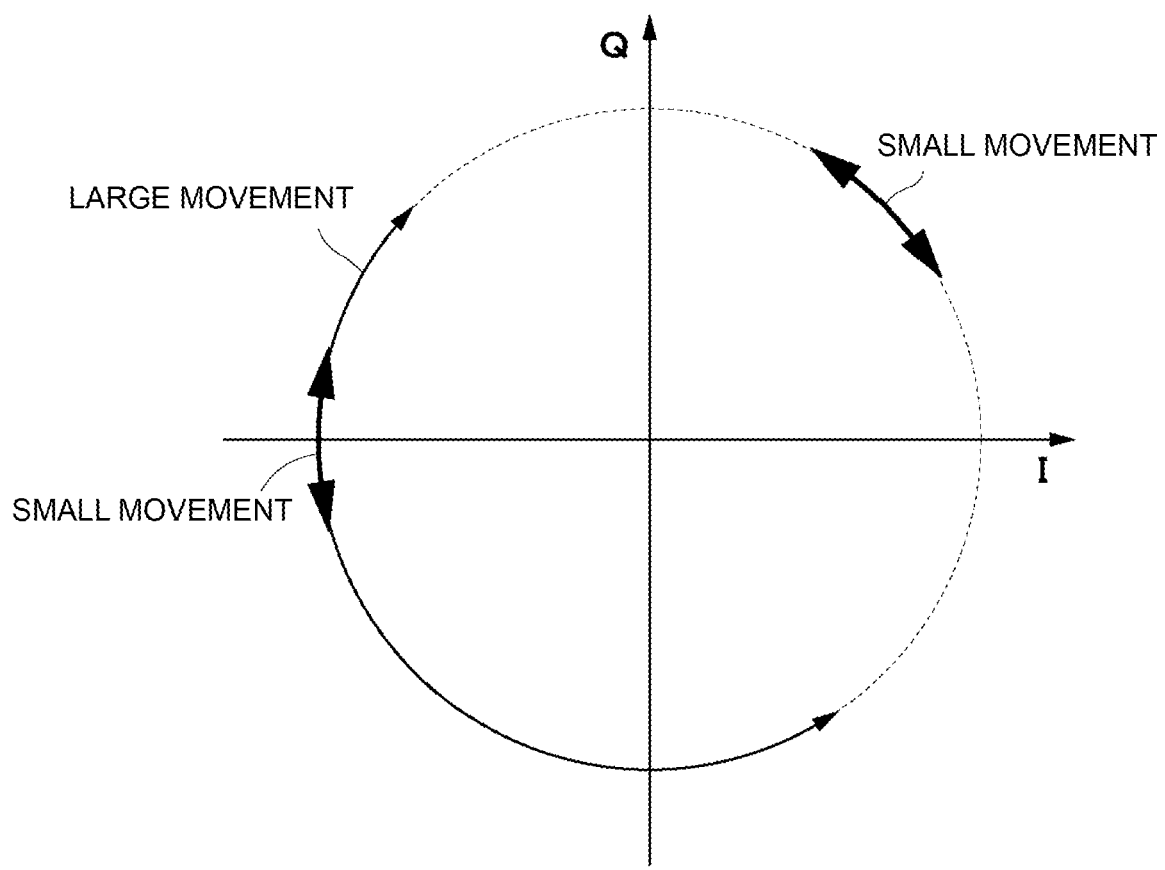
FIG. 2 is a diagram describing the movement of a reception signal on an IQ plane.

FIG. 2 illustrates an example of an output signal (an I signal and a Q signal) of the heartbeat measurement device 1 (the orthogonal detection circuit 7). With the movement of a target (for example, the chest surface of the person to be measured O), the phase of the reception signal Sr rotates and the signal moves on the circumference of a circle on an IQ plane. When the distance between the heartbeat measurement device 1 and the person to be measured O changes by the half wavelength of the transmission signal St, the signal makes one circle on the IQ plane. When the heartbeat measurement device 1 and the person to be measured O move closer to each other, the signal rotates counterclockwise on the IQ plane. When the heartbeat measurement device 1 and the person to be measured O move away from each other, the signal rotates clockwise on the IQ plane. When the amount of change in the distance between the heartbeat measurement device 1 and the person to be measured O is sufficiently shorter than the half wavelength of the transmission signal St, the movement of the locus illustrated in FIG. 2 is performed on only a part of the circumference of the circle and is substantially linear.

Figure 3A:
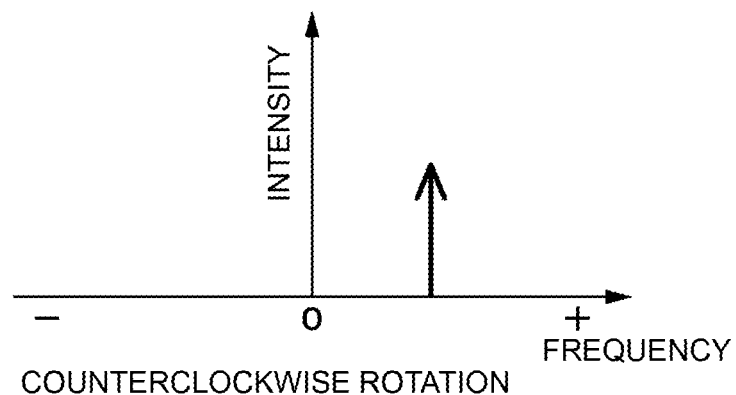
FIGS. 3A, 3B, and 3C are diagrams describing the relationship between the movement of a person to be measured and a spectrum.
Figure 3B:
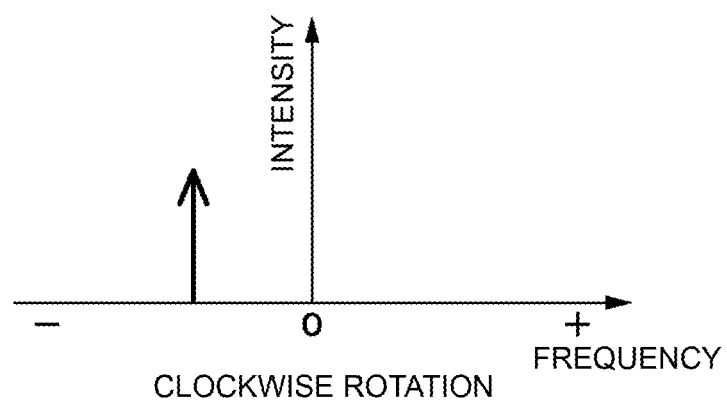
Figure 3C:
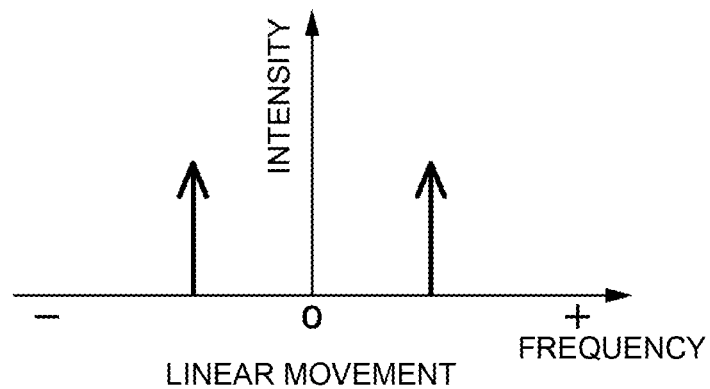

FIGS. 3A-3C illustrate frequency components in a spectrum obtained by performing Fourier transform upon an IQ signal. When the movement of the person to be measured O is large, the signal moves on the circumference of a circle on an IQ plane as illustrated in FIG. 2. When the heartbeat measurement device 1 and the person to be measured O move closer to each other and the signal rotates counterclockwise on an IQ plane, frequency components in the spectrum Ss appear as positive frequency components as illustrated in FIG. 3A. When the heartbeat measurement device 1 and the person to be measured O move away from each other and the signal rotates clockwise on the IQ plane, frequency components in the spectrum Ss appear as negative frequency components as illustrated in FIG. 3B. When the movement of the person to be measured O is small, substantially the same components are obtained on the positive and negative sides as illustrated in FIG. 3C.

FIG. 4 illustrates an example of the spectrum Ss of the reception signal Sr (an I signal and a Q signal) generated on the basis of a heartbeat. The frequency f0 of the transmission signal St is in the range of 10 GHz to 100 GHz. Accordingly, the wavelength of the transmission signal St is in the range of 3 mm to 30 mm, and the half wavelength of the transmission signal St is in the range of 1.5 mm to 15 mm. At that time, the movement amount of a chest surface which occurs because of a heartbeat is in the range of approximately 0.5 mm to 1.0 mm and is less than the half wavelength of the transmission signal St. The movement of the locus illustrated in FIG. 2 is therefore performed on only a part of the circumference of the circle and is substantially linear. As a result, as illustrated in FIG. 4, the spectrum Ss of a heartbeat has substantially the same frequency components on the positive and negative sides.

An I signal and a Q signal are divided by the time width Tw and are subjected to Fourier transform. Portions of the I signal and the Q signal into which the I signal and the Q signal are divided by the time width Tw are slightly shifted. Since the portions of the I signal and the Q signal which are subjected to Fourier transform are shifted, a signal intensity in the spectrum Ss changes over time. The amplitudes of points having substantially the same frequency components on the positive and negative sides in the spectrum Ss of a heartbeat are substantially the same. Accordingly, the signal processing unit 9 can extract a heartbeat signal by extracting positive and negative frequency components whose signal intensities are in the same range.

Thus, the Fourier transform unit 8 calculates the spectrum Ss in positive and negative frequency domains on the basis of an I signal and a Q signal of a wave (the reception signal Sr) reflected from the person to be measured O. The signal processing unit 9 compares positive and negative frequency components in the spectrum Ss to extract a heartbeat component. At that time, the frequency component of a signal based on small movement, such as a heartbeat appears in the positive and negative frequency domains in substantially the same manner. In contrast, a signal based on large movement, such as body motion has different positive and negative frequency components. The signal processing unit 9 can therefore extract a signal based on a heartbeat by comparing positive and negative frequency components in the spectrum Ss and extracting the same component in the positive and negative frequency domains. As a result, a signal based on a heartbeat and a signal based on body motion can be separated. Even if there is an effect by body motion, a heartbeat component can be accurately extracted.

Since the frequency of the transmission signal St is in the range of 10 GHz to 100 GHz, the wavelength of the transmission signal St is in the range of 3 mm to 30 mm and the half wavelength of the transmission signal St is in the range of 1.5 mm to 15 mm. At that time, the movement amount of a chest surface which occurs because of a heartbeat is in the range of approximately 0.5 mm to 1.0 mm and is less than the half wavelength of the transmission signal St. On the other hand, the movement amount of a chest surface which occurs because of a breath is approximately 10 mm and is substantially equal to the half wavelength of the transmission signal St. Accordingly, by setting the frequency of the transmission signal St in the range of 10

GHz to 100 GHz, a heartbeat can be detected as small movement and a breath can be detected as large movement. A heartbeat and a breath can be accurately separated.

The spectrum computation unit is formed by the Fourier transform unit 8 for performing Fourier transform upon an I signal and a Q signal. There are a time period in which a chest surface instantaneously vibrates during a single heartbeat and a time period in which the chest surface hardly moves. Since the time width Tw used in Fourier transform is set to be shorter than the heartbeat interval Thb, the Fourier transform unit 8 can accurately observe the time change in a frequency component and observe respective heartbeats in chronological order. Heart beat detection accuracy is therefore improved.

Figure 5:
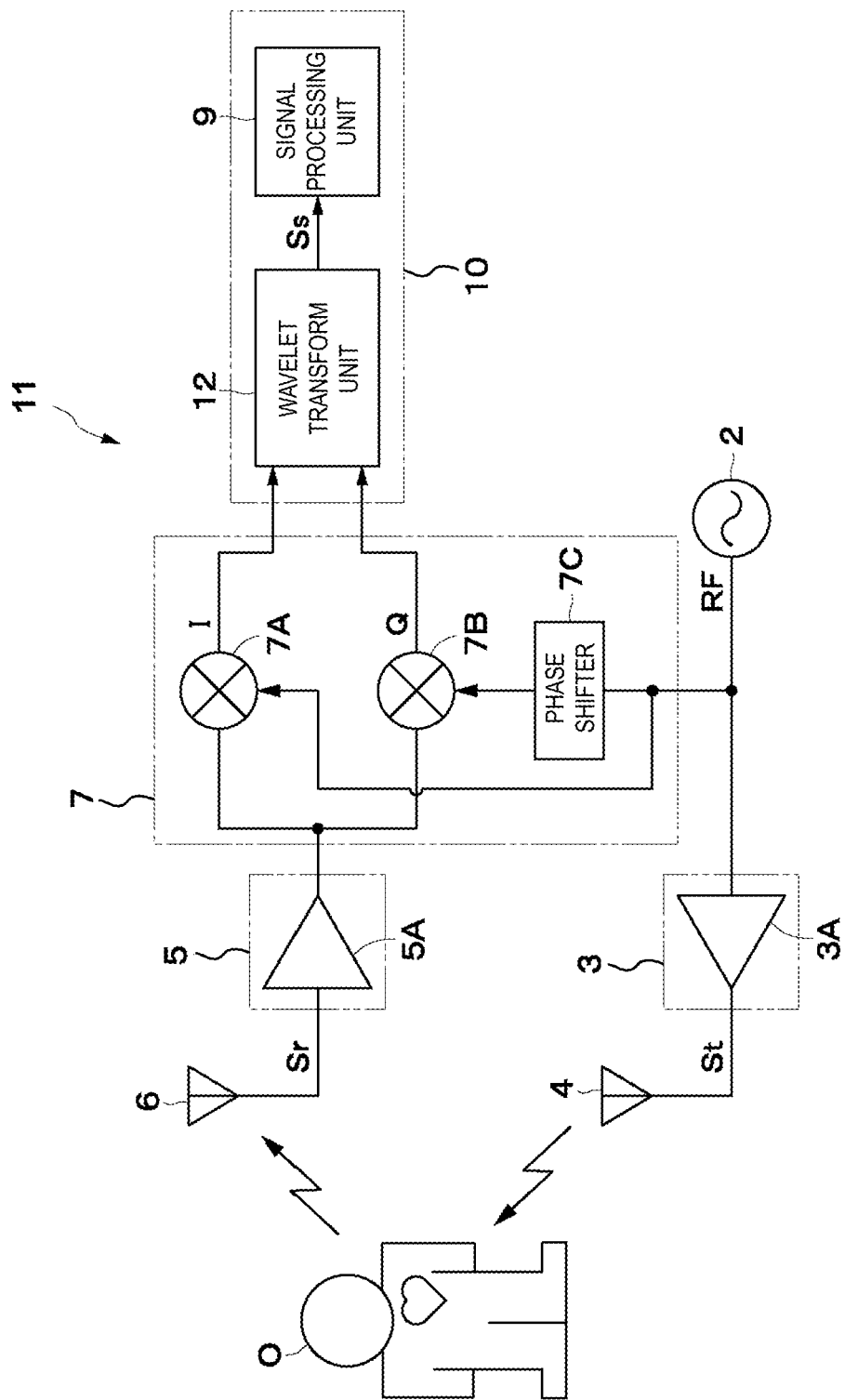
FIG. 5 is a block diagram illustrating the configuration of a heartbeat measurement device according to a second embodiment of the present disclosure.

Next, FIG. 5 illustrates a heartbeat measurement device 11 according to a second embodiment of the present disclosure. The feature of the second embodiment is that the spectrum computation unit includes a wavelet transform unit for performing wavelet transform upon an I signal and a Q signal. In the description of the heartbeat measurement device 11, the same reference numeral is used to represent the same component or the same part in the heartbeat measurement device 1 according to the first embodiment so as to avoid repeated explanation.

The heartbeat measurement device 11 includes the transmitter 3, the receiver 5, the orthogonal detection circuit 7, the wavelet transform unit 12, the signal processing unit 9, and other components.

The wavelet transform unit 12 and the signal processing unit 9 are formed by, for example, the arithmetic device 10 such as a microcomputer. The arithmetic device 10 executes various programs to operate as the wavelet transform unit 12 and the signal processing unit 9.

The wavelet transform unit 12 forms a spectrum computation unit for calculating the spectrum Ss in positive and negative frequency domains on the basis of an I signal and a Q signal. The wavelet transform unit 12 changes a time width on the basis of a frequency band to be analyzed at the time of Fourier transform. Specifically, the wavelet transform unit 12 sets a wide time width for a low frequency band and a narrow time width for a high frequency band. Signal analysis can therefore be performed in a wide frequency band at the same time.

Data that has been subjected to Fourier transform has positive and negative frequency domains. The wavelet transform unit 12 calculates a frequency component in a signal with a variable time width and continuously outputs the time change in the frequency component. The wavelet transform unit 12 outputs the spectrum Ss to the signal processing unit 9.

Also in the second embodiment, an operational effect similar to that obtained in the first embodiment can be obtained. The spectrum computation unit includes the wavelet transform unit 12 for performing wavelet transform upon an I signal and a Q signal. The wavelet transform unit 12 changes a time width on the basis of a frequency band to be analyzed at the time of Fourier transform. The wavelet transform unit 12 can therefore perform signal analysis in a wide frequency band at the same time by setting a wide time width for a low frequency band and a narrow time width for a high frequency band.

Next, FIG. 6 illustrates a heartbeat measurement device 21 according to a third embodiment of the present disclosure. The feature of the third embodiment is that a single transmission/reception antenna functioning as both a transmission antenna and a reception antenna is provided. In the description of the heartbeat measurement device 21, the same reference numeral is used to represent the same component or the same part in the heartbeat measurement device 1 according to the first embodiment so as to avoid repeated explanation.

The heartbeat measurement device 21 includes the transmitter 3, the receiver 5, the orthogonal detection circuit 7, the Fourier transform unit 8, the signal processing unit 9, and other components. The transmitter 3 and the receiver 5 are connected to a transmission/reception antenna 23 via a circulator 22.

The transmission/reception antenna 23 is used for both the transmission of the transmission signal St and the reception of the reception signal Sr. The transmission/reception antenna 23 includes various antennas capable of emitting the transmission signal St and receiving the reception signal Sr that is a reflected wave of the transmission signal St. The circulator 22 supplies the transmission signal St output from the transmitter 3 to the transmission/reception antenna 23 and transmits the reception signal Sr received from the transmission/reception antenna 23 to the receiver 5.

Also in the third embodiment, an operational effect similar to that obtained in the first embodiment can be obtained. The transmission/reception antenna 23 functioning as both a transmission antenna and a reception antenna is provided. As compared with a case where a transmission antenna and a reception antenna are separately provided, the entire device can be downsized.

The heartbeat measurement device 21 according to the third embodiment includes the Fourier transform unit 8 according to the first embodiment, but may include the wavelet transform unit 12 according to the second embodiment.

As illustrated in FIG. 7, the heartbeat measurement device 1 may be installed in a vehicle V. In this case, the transmitter 3 and the receiver 5 are installed in the vehicle V. Specifically, the transmitter 3 and the receiver 5 are disposed at a position opposing a driver D, for example, around a steering wheel S of the vehicle V. The transmitter 3 transmits the transmission signal St to the driver D of the vehicle V who is a person to be measured. The receiver 5 receives a signal reflected from the driver D as the reception signal Sr. As a result, the heartbeat of the driver D of the vehicle V can be detected. The heartbeat measurement device 1 according to the first embodiment does not necessarily have to be installed in the vehicle V. The heartbeat measurement device 11 according to the second embodiment or the heartbeat measurement device 21 according to the third embodiment may be installed in the vehicle V.

It is to be noted that the above-described embodiments are merely illustrative and the configurations described in the different embodiments may be partly replaced or combined.

Next, disclosures included in the above-described embodiments will be described. A heartbeat measurement device according to the present disclosure including a transmission unit configured to transmit a transmission signal from a transmission antenna to a person to be measured, a reception unit configured to receive a signal reflected from the person to be measured as a reception signal using a reception antenna, and a signal generation unit configured to generate an I signal that is an in-phase component of the transmission signal and the reception signal and a Q signal that is a quadrature component of the transmission signal and the reception signal includes a spectrum computation unit configured to calculate a spectrum in positive and negative frequency domains on the basis of the I signal and the Q signal and a signal processing unit configured to compare positive and negative frequency components in the spectrum to extract a heartbeat component.

According to the present disclosure, the spectrum computation unit calculates a spectrum in positive and negative frequency domains on the basis of the I signal and Q signal of a wave reflected from a person to be measured. The signal processing unit compares positive and negative frequency components in the spectrum to extract a heartbeat component. At that time, the frequency component of a signal based on small movement, such as a heartbeat appears in the positive and negative frequency domains in substantially the same manner. In contrast, a signal based on large movement, such as body motion has different positive and negative frequency components. The signal processing unit can therefore extract a signal based on a heartbeat by comparing positive and negative frequency components in a spectrum and extracting the same component in the positive and negative frequency domains. As a result, a signal based on a heartbeat and a signal based on body motion can be separated. Even if there is an effect by body motion, a heartbeat component can be accurately extracted.

In the present disclosure, a frequency of the transmission signal is in a range of 10 GHz to 100 GHz.

According to the present disclosure, the frequency of the transmission signal is in the range of 10 GHz to 100 GHz. The wavelength of the transmission signal is therefore in the range of 3 mm to 30 mm and the half wavelength of the transmission signal is therefore in the range of 1.5 mm to 15 mm. At that time, the movement amount of a chest surface which occurs because of a heartbeat is in the range of approximately 0.5 mm to 1.0 mm and is less than the half wavelength of the transmission signal. On the other hand, the movement amount of a chest surface which occurs because of a breath is approximately 10 mm and is substantially equal to the half wavelength of the transmission signal. By setting the frequency of the transmission signal in the range of 10 GHz to 100 GHz, a heartbeat can be detected as small movement and a breath can be detected as large movement. A heartbeat and a breath can be accurately separated.

In the present disclosure, the spectrum computation unit is a Fourier transform unit configured to set a time width shorter than a heartbeat interval and perform a Fourier transform upon the I signal and the Q signal.

There are a time period in which a chest surface instantaneously vibrates during a single heartbeat and a time period in which the chest surface hardly moves. Since a time width used in a Fourier transform is set to be shorter than a heartbeat interval, the Fourier transform unit can accurately observe the time change in a frequency component and observe respective heartbeats in chronological order. Heart beat detection accuracy is therefore improved.

In the present disclosure, the spectrum computation unit is a wavelet transform unit configured to perform wavelet transform upon the I signal and the Q signal.

The wavelet transform unit changes a time width on the basis of a frequency band to be analyzed at the time of Fourier transform. The wavelet transform unit can therefore perform signal analysis in a wide frequency band at the same time by setting a wide time width for a low frequency band and a narrow time width for a high frequency band.

In the present disclosure, the transmission antenna and the reception antenna are provided in a form of a single transmission/reception antenna functioning as both the transmission antenna and the reception antenna.

As compared with a case where a transmission antenna and a reception antenna are separately provided, the entire device can be downsized.

In the present disclosure, the transmission unit and the reception unit are installed in a vehicle, the transmission unit transmits the transmission signal to a driver of the vehicle who is the person to be measured, and the reception unit receives a signal reflected from the driver as the reception signal. As a result, the heartbeat of the driver of the vehicle can be detected.

REFERENCE SIGNS LIST 1, 11, and 21 heartbeat measurement device
3 transmitter (transmission unit)
4 transmission antenna
5 receiver (reception unit)
6 reception antenna
7 orthogonal detection circuit (signal generation unit)
8 Fourier transform unit (spectrum computation unit)
9 signal processing unit
12 wavelet transform unit (spectrum computation unit)
23 transmission/reception antenna

The invention claimed is:

1. A heartbeat measurement device comprising:
a transmitter configured to transmit a transmission signal from a transmission antenna to a person;
a receiver configured to receive, with a reception antenna, a signal reflected from the person as a reception signal;
a signal generator configured to generate an I signal that is an in-phase component of the transmission signal and the reception signal, and a Q signal that is a quadrature component of the transmission signal and the reception signal; and
at least one processor configured to:
calculate a spectrum in positive and negative frequency domains based on the I signal and the Q signal;
compare positive and negative frequency components in the spectrum; and
extract a heartbeat component based on the comparison.

2. The heartbeat measurement device according to claim 1, wherein a frequency of the transmission signal is between 10 GHz and 100 GHz.

3. The heartbeat measurement device according to claim 2, wherein the at least one processor is further configured to perform a Fourier transform on the I signal and the Q signal based on a time width that is less than a heartbeat interval.

4. The heartbeat measurement device according to claim 2, wherein the at least one processor is further configured to perform a wavelet transform on the I signal and the Q signal.

5. The heartbeat measurement device according claim 2, wherein the transmission antenna and the reception antenna are constituted as a single transmission/reception antenna.

6. The heartbeat measurement device according to claim 2,
wherein the transmitter and the receiver are installed in a vehicle, and
wherein the person is a driver of the vehicle.

7. The heartbeat measurement device according to claim 1, wherein the at least one processor is further configured to perform a Fourier transform on the I signal and the Q signal based on a time width that is less than a heartbeat interval.

8. The heartbeat measurement device according claim 7, wherein the transmission antenna and the reception antenna are constituted as a single transmission/reception antenna.

9. The heartbeat measurement device according to claim 7, wherein the transmitter and the receiver are installed in a vehicle, and wherein the person is a driver of the vehicle.

10. The heartbeat measurement device according to claim 1, wherein the at least one processor is further configured to perform a wavelet transform on the I signal and the Q signal.

11. The heartbeat measurement device according claim 10, wherein the transmission antenna and the reception antenna are constituted as a single transmission/reception antenna.

12. The heartbeat measurement device according to claim 10, wherein the transmitter and the receiver are installed in a vehicle, and wherein the person is a driver of the vehicle.

13. The heartbeat measurement device according claim 1, wherein the transmission antenna and the reception antenna are constituted as a single transmission/reception antenna.

14. The heartbeat measurement device according to claim 13, wherein the transmitter and the receiver are installed in a vehicle, and wherein the person is a driver of the vehicle.

15. The heartbeat measurement device according to claim 13, wherein the transmitter and the receiver are installed in a vehicle, and wherein the person is a driver of the vehicle.

* * * * *